United States Patent
Deka et al.

(10) Patent No.: US 7,449,337 B2
(45) Date of Patent: Nov. 11, 2008

(54) LYTIC REAGENT AND METHOD FOR LEUKOCYTES DIFFERENTIAL IN WHOLE BLOOD

(75) Inventors: Chiranjit Deka, Falmouth, ME (US); Jianwen Feng, Newton, MA (US)

(73) Assignee: IDEXX Laboratories, Inc., Westbrook, MA (US)

( * ) Notice: Subject to any disclaimer, the term of this patent is extended or adjusted under 35 U.S.C. 154(b) by 0 days.

(21) Appl. No.: 11/626,759

(22) Filed: Jan. 24, 2007

(65) Prior Publication Data

US 2008/0176331 A1     Jul. 24, 2008

(51) Int. Cl.
G01N 31/00 (2006.01)
G01N 33/48 (2006.01)

(52) U.S. Cl. .............. 436/17; 436/8; 436/10; 436/18; 436/63; 436/73; 436/79; 436/164; 436/166; 436/174; 436/175; 252/408.1; 422/73; 422/82.05; 422/82.09; 435/2

(58) Field of Classification Search .............. 436/8, 436/10, 17, 18, 63, 73, 79, 164, 166, 174, 436/175; 435/2; 252/408.1; 422/73, 82.05, 422/82.09
See application file for complete search history.

(56) References Cited

U.S. PATENT DOCUMENTS

| | | | |
|---|---|---|---|
| 4,286,963 A | | 9/1981 | Ledis et al. |
| 4,485,175 A | | 11/1984 | Ledis et al. |
| 4,528,274 A | * | 7/1985 | Carter et al. ............. 436/10 |
| 4,637,986 A | | 1/1987 | Brown et al. |
| 4,978,624 A | * | 12/1990 | Cremins et al. ............. 436/17 |
| 5,116,539 A | | 5/1992 | Hamaguchi et al. |
| 5,155,044 A | | 10/1992 | Ledis et al. |
| 5,196,346 A | | 3/1993 | Lefevre et al. |
| 5,384,549 A | | 1/1995 | Araki |
| 5,510,267 A | | 4/1996 | Marshall |
| 5,538,893 A | * | 7/1996 | Sakata et al. ............. 436/10 |
| 5,639,630 A | * | 6/1997 | Malin et al. ............. 435/28 |
| 5,786,224 A | * | 7/1998 | Li et al. ............. 436/63 |
| 5,817,518 A | | 10/1998 | Li et al. |
| 6,200,500 B1 | * | 3/2001 | Ryan ............. 252/408.1 |
| 6,210,969 B1 | * | 4/2001 | Li et al. ............. 436/10 |
| 6,232,125 B1 | * | 5/2001 | Deka et al. ............. 436/63 |
| 6,630,990 B2 | * | 10/2003 | van't Oever et al. ......... 356/39 |
| 6,858,439 B1 | | 2/2005 | Xu et al. |
| 6,869,798 B2 | | 3/2005 | Crews et al. |
| 6,890,756 B2 | * | 5/2005 | Wu ............. 436/66 |
| 2005/0048477 A1 | | 3/2005 | Peng et al. |

FOREIGN PATENT DOCUMENTS

| | | | |
|---|---|---|---|
| CN | 1706959 | * | 12/2005 |
| DE | 19941359 | | 3/2001 |
| EP | 0 743 519 A | | 11/1996 |
| EP | 1 004 880 A | | 5/2000 |
| WO | 0197785 | | 12/2001 |

OTHER PUBLICATIONS

International Search Report dated Apr. 29, 2008.
Klessig D. F. et al,: "Block to Multiplication of Adenovirus Serotype 2 in Monkey Cells." J Virol, vol. 16, No. 6, Dec. 1975, pp. 1650-1668, XP002478609.
Anderson, S. A. et al.: "Molecular Cloning of the Glycosomal Malate Dehydrogenase of Trypanosoma Brucei." Mol Blochem Parasitol, vol. 96, No. 1-2, Oct. 30, 1998, pp. 185-189, XP002478610.
Marie, D., et al.: "DNA/RNA Analysis of Phytoplankton by Flow Cytometry" Current Protocols in Cytometry, vol. 11, No. 12. Jan. 2000 pp. 11.12.1-11.12.14, XP002478611.

* cited by examiner

*Primary Examiner*—Maureen M Wallenhorst
(74) *Attorney, Agent, or Firm*—Carter, DeLuca, Farrell & Schmidt, LLP

(57) ABSTRACT

A lytic reagent composition and methods for differential analysis of leukocytes are disclosed. In embodiments, the analysis may utilize optical measurements in flow cytometry based hematology analyzers. The reagent system includes an anionic surfactant in a hypotonic solution, an inorganic buffer to maintain the pH in a range from about 6 to about 10, and optionally a leukocyte stabilizer. The reagent system is used to lyse red blood cells and stabilize the leukocytes to enable multi-part differentiation of leukocytes in a near physiologic pH environment on a flow cytometry based hematology analyzer using axial light loss, light scatter intensity, high-numerical aperture side scatter, and time-of-flight measurements.

23 Claims, 5 Drawing Sheets

LYTIC REAGENT AND METHOD FOR LEUKOCYTES DIFFERENTIAL IN WHOLE BLOOD

BACKGROUND

1. Technical Field

The present disclosure relates to a reagent system for differentiation of leukocyte sub populations in whole blood. In embodiments, the reagent system may be utilized with an automated flow cytometry based hematology analyzer.

2. Background of Related Art

Analysis of the leukocyte subpopulation in a blood sample is an important step in clinical pathology. It provides important information for diagnosis of pathological infection and disease, and is useful in monitoring progress in recovery of patients following treatment.

Leukocytes are any of several types of blood cells that help with defending the body from infection. The different mature forms include granulocytes, including neutrophils (heterophils), basophils, and eosinophils; monocytes, including macrophages; and lymphocytes. These mature forms have different functions, including ingesting bacteria, protozoans, or infected or dead body cells; producing antibodies; and regulating the action of other leukocytes. They act mostly in the tissues. Blood normally contains about 5,000-10,000 leukocytes per cubic millimeter.

Traditional methods for blood analysis involve staining a blood sample with vital stains and counting individual cells on a slide under a microscope to determine the absolute number and percentage of various sub populations within a whole blood sample. For accuracy and reliability, this approach is dependent on the skill and experience of the technologist making the slides and counting the cells. In addition, the method is time consuming and often lacks statistical robustness as only a few hundred cells may be counted per sample. Automated hematology analyzers, based on flow cytometry technology, offer an improvement over the limitations of the manual method by counting thousands of cells within seconds.

A pre-requisite for automated leukocyte analysis is the lysis of red blood cells (RBC) prior to measurement and stabilization of the white blood cells (WBC) during the measurement of each sample. In addition, in order for the different sub populations of the WBC to be analyzed individually, the morphological differences between these populations must be maintained and/or enhanced for effective response by the detector system used for the analysis. For measurement systems based on electrical impedance (i.e., Coulter Principle), size differences are of utmost importance in distinguishing one population from another. For light scatter based measurements, resolution between individual leukocyte sub populations depends on a complex combination of size, internal structure, and relative refractive indices of the cellular material. As a result, whether or not a reagent system can enable accurate identification and analysis of individual leukocyte sub populations after removal of the RBC by lysis can only be determined by experimentation.

Improved reagent systems for blood analysis remain desirable. Such a system should allow rapid, one-step multi-part leukocyte differential analysis of whole blood, in embodiments, in an automated hematology analyzer. The reagent conditions should be neither too acidic nor too alkaline, preferably, in near physiologic pH environment using fewer optical detectors. The reagents and analyzer should not subject the leukocytes to harsh reagent conditions that can degrade one or more of the leukocyte sub populations.

SUMMARY

The reagent system of the present disclosure may be useful for differential analysis of leukocytes, in embodiments, using automated optical measurements in a flow cytometric hematology analyzer. The reagent system includes an anionic surfactant, an alkaline metal salt used to adjust osmolality from about 15 to about 150 milliosmoles (mOsm), and a buffer that maintains a pH from about 6 to about 10.

The present disclosure also provides a hypertonic solution for discontinuing a lytic reaction which includes an alkaline chloride salt possessing an alkaline ion such as sodium, potassium and/or lithium.

The present disclosure also provides methods for resolving white blood cells in a whole blood sample. The methods include providing a sample of whole blood in a flow cytometer which is incubated for lysis of RBC with the reagent system of the present disclosure. The blood sample may then be contacted with the hypertonic solution and a response of at least two detectors may be obtained as the white blood cells pass through a sensing region in a flow cell.

BRIEF DESCRIPTION OF THE DRAWINGS

Various embodiments of the present disclosure will be described herein below with reference to the figures wherein.

DETAILED DESCRIPTION

Figure 1:
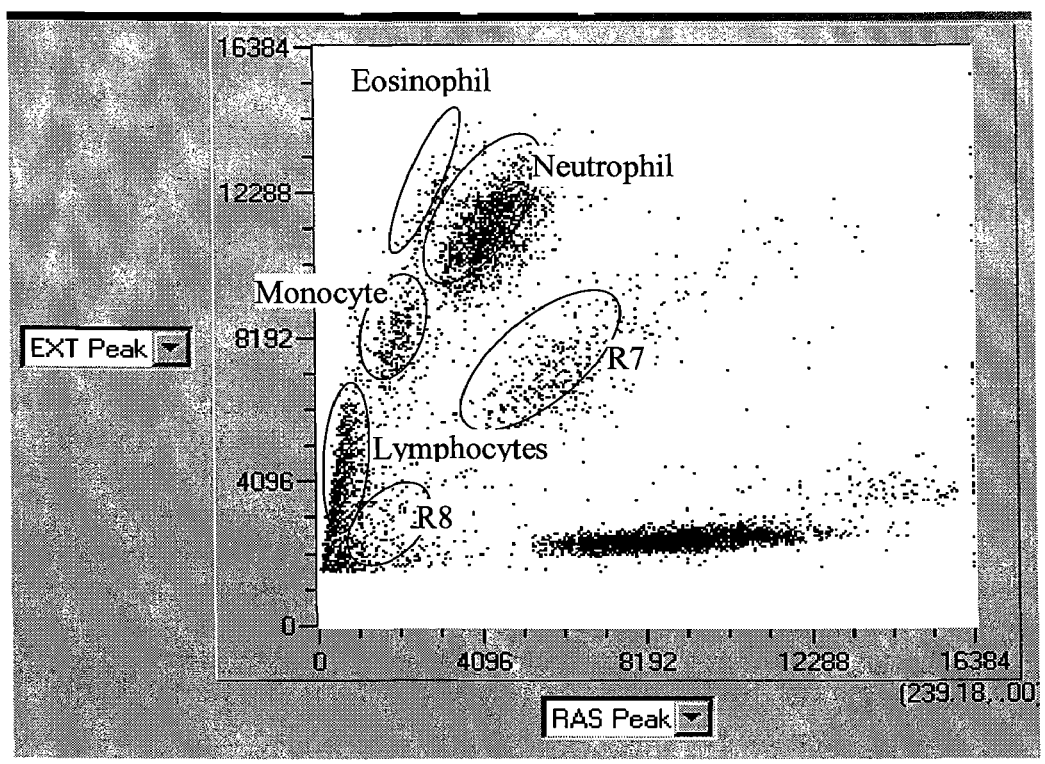
FIG. 1 is a dot plot depicting the components of a blood sample utilizing a prior art reagent system.

In general, the present disclosure provides a lytic reagent system for differential analysis of leukocytes. In embodiments, the lytic reagent system may be utilized in automated systems using optical measurements, including flow cytometric hematology analyzers. The reagent system includes an anionic surfactant that serves the dual function of lysing red blood cells (RBCs) and solubilizing debris, an alkaline metal salt used to adjust osmolality, and an inorganic buffer to maintain the pH of the reagent system from about 6 to about 10.

Suitable anionic surfactants of the lytic reagent system of the present disclosure include alkaline alkyl sulfates, alkaline alkyl carbonates, and alkaline alkyl phosphates, with the alkyl chains containing from about 4 to about 20 carbons, in embodiments from about 8 to about 14 carbons. The alkaline moiety of the anionic surfactants may be provided by any alkali metal, including (Li), sodium (Na), and potassium (K). Suitable alkaline alkyl sulfates include, for example, sodium alkyl sulfate (SAS), sodium lauryl or dodecyl sulfate (SLS or SDS), ammonium lauryl or dodecyl sulfate (ALS or ADS), combinations thereof, and the like. Suitable alkaline alkyl carbonates include, for example, sodium alkyl carbonate (SAC), ammonium alkyl carbonate (AAC), potassium alkyl carbonate (PAC), combinations thereof, and the like. Suitable alkaline alkyl phosphates include, for example, sodium alkyl phosphate (SAP), potassium alkyl phosphate (PAP), combinations thereof, and the like. One advantage of using the anionic surfactant is that it can serve dual functions as both a lytic agent and debris solubilizer.

Suitable sodium alkyl sulfates which may be utilized as the anionic surfactant include, for example, sodium octyl sulfate, sodium dodecyl sulfate (SDS), combinations thereof, and the like. Suitable sodium alkyl carbonates which may be utilized as the anionic surfactant include, for example, sodium oleate (SO). Suitable sodium alkaline alkyl phosphates which may be utilized as the anionic surfactant include, for example, Triton QS-44 (polyether phosphate ester).

The function of the anionic surfactant, SDS for example, in the present lytic reagent system is to break down RBC membrane and solubilize protein and hydrophobic composition of membrane, such as sterols, phospholipids, carbohydrates, and the like, to remove cell debris while not adversely affecting the WBC from lysis. The additional advantage of SDS is to prevent lysed RBC membranes from forming ghost cells, which can be part of small fragments on a scattering plot. Due to its strong lytic activity, the concentration of the anionic surfactant may be from about 0.005% to about 0.015%, in embodiments from about 0.01% to about 0.0125%, in aqueous solution.

As noted above, the reagent system of the present disclosure also possesses an alkaline metal salt to adjust osmolality of the reagent system. Suitable alkaline metal salts include, for example, alkaline halides, including chlorides, bromides, iodides, and the like. In embodiments, the alkaline metal salts may include alkaline chlorides. Suitable alkaline chlorides include, but are not limited to, sodium chloride (NaCl), lithium chloride (LiCl), potassium chloride (KCl), and/or combinations thereof. A suitable salt concentration or osmolality may be important for proper lysis of the RBC and resolution of WBC populations, particularly the eosoniphils from neutrophils. The salt concentration in the lytic reagent can be from about 3 to about 50 mM, in embodiments from about 6 to about 35 mM.

As noted above, the reagent system of the present disclosure also contains a buffer to maintain a desired pH. Suitable buffers include any physiologic buffers such as, for example, phosphate and Tris base buffers. The concentration of the buffer may be from about 2 to about 10 mM, in embodiments from about 3 to about 7 mM, in some embodiments about 5 mM. Utilizing these buffers, the pH of the reagent system may be maintained from about 6 to about 10, in embodiments from about 7 to about 9, and in other embodiments from about 7.2 to about 8. This near physiological pH is good for stabilizing white blood cells in a natural condition.

In embodiments, it may also be desirable to include a stabilizer, sometimes referred to herein as a leukocyte stabilizing agent, in the reagent system of the present disclosure during the lysis of RBC. Suitable stabilizers include, for example, bovine serum albumin (BSA), and the like. Other stabilizers that can be used to bind molecules to the support include polysaccharides. The stabilizer may be added to provide additional leukoprotective function at a concentration of from about 0.01 to about 0.2%, in embodiments from about 0.08% to about 0.13% in deionized water.

In embodiments, an SAS such as sodium dodecyl sulfate (SDS) may be used in the reagent system. In other embodiments, an SAC may be utilized in the lytic reagent system, such as sodium oleate (SO). In yet other embodiments, an SAP may be utilized in the lytic reagent system, such as Triton QS-44 (polyether phosphate ester).

The above surfactants may be present at a concentration of from about 0.005% to about 0.015% (w/v) in a hypotonic aqueous solution of an alkaline salt such as NaCl, KCl and LiCl, maintaining the osmolality from about 15 to about 150 mOsm, in embodiments from about 25 to about 80 mOsm. In embodiments, a buffer may be added to adjust the pH of the reagent from about 6 to about 10, in embodiments from about 7 to about 9. BSA may optionally be added, which acts as a secondary stabilizer for the leukocytes.

In other embodiments, the present reagent system may include an isotonic sheath. The isotonic sheath is a fluid specifically formulated for use in flow cytometers and is intended for use as the delivery medium of the sample to the optics component of a flow cytometer. The isotonic sheath fluid is carefully manufactured for low particle and fluorescence backgrounds to ensure superior signal to noise ratio measurements and to enhance particle identification.

The reagent may optionally include a hypertonic, stop reagent to permit analysis of the WBC over a longer period of time in their near native state where no structural damage to the outside membrane or internal structures of the cell are observable. The stop reagent composition includes an aqueous buffer solution with alkali metal salts. Examples of alkali metal salts include but are not limited to NaCl, LiCl, KCl, and/or combinations thereof. The concentration of salts can vary and depends on the volume added into the lysed samples. In embodiments, the hypertonic stop reagent/solution may have alkaline salts present at a concentration from about 150 mM to about 250 mM, in embodiments from about 175 mM to about 225 mM.

The stop reagent may be added subsequent to the lysis of red blood cells to stop further lytic activity and prevent lysis of white blood cells. This is done so that the lytic reagent system can be applied to temperatures up to about 35° C., in embodiments from about 20° C. to about 33° C. In one embodiment, the incubation period is from about 5 to about 60 seconds, in embodiments from about 8 to about 45 seconds, and in other embodiments from about 10 to about 30 seconds.

The addition of the stop reagent may provide a stabilizing effect on the leukocytes and also provide sufficient time for analysis, in embodiments from about 60 seconds to about 15 minutes, in other embodiments from about 2 minutes to about 10 minutes.

The present disclosure also provides a method for rapid leukocyte differential analysis using the lytic reagent system of the present disclosure. In embodiments, the reagent system of the present disclosure may be utilized with a flow cytometer.

In a flow cytometer, a fluid that contains a known amount of particles per unit volume passes by a sensor. When external energy such as light from a laser, or electromagnetic radiation from an electromagnet, is directed into such a flowing fluid, the particles will scatter, absorb or reemit such energy dependent on characteristics peculiar to such particles. Scattered, absorbed or reemitted energy can be measured by a sensor. The exact amount of such energy received by a sensor per unit time gives a direct indication of the quantity of particles that have passed by in the stream. By knowing the number of such particles per unit volume, the amount of volume per unit time that has passed by can be calculated with an automated instrument (the flow rate). In embodiments, suitable flow cytometer detection systems include, for example, the optical detection system of LASERCYTE® hematology analyzer, (commercially available from IDEXX Laboratories Inc.), and flow cytometers described in U.S. Patent Publication No. 2004/0246480 and 20060203226, the entire disclosures of which are incorporated by reference herein. These flow cytometers may utilize extinction or axial light loss (EXT), low angle forward light scatter (FSL), right angle scatter (RAS) channels, high angle forward light scatter (FSH) and time-of-flight (TOF) channels for measuring the signals from the WBC in a flow cell as the cells pass through a sensing region.

The reagent system may be maintained in near-physiologic pH conditions from about 6 to about 10, in embodiments from about 7 to about 9, in other embodiments from about 7.2 to about 8, to maintain leukocytes in their native states while incubating the whole blood sample for lysis of RBC. The WBC may then be contacted with the hypertonic solution to provide measurements from two optical detectors capable of measuring axial light loss, side scatter, and time of flight, for example, in the flow cytometer as the cells pass through a sensing region, the first optical detector providing a measure of axial light loss and time of flight and the second optical detector providing a measure of side scatter. In another embodiment, the present reagent system and method can optionally be used with more than two light scatter detectors.

The lytic reagent system provides a method capable of conducting leukocyte differential on blood samples from multiple animal species including, but not limited to, canine, feline, equine, bovine, murine, ferret, mouse, rat and human.

In another embodiment, the lytic reagent system includes an optional additive such as bioactive agents. Suitable bioactive agents include, for example, biocide agents, antibiotics, antimicrobial agents, medicaments, growth factors, anti-clotting agents, analgesics, anesthetics, anti-inflammatory agents, and combinations thereof.

By applying the lytic reagent system of the present disclosure into whole blood samples, leukocytes may be easily differentiated into four subpopulations: lymphocytes, monocytes, neutrophils and eosinophils. The reagent system may be utilized with any suitable blood analysis system, including flow cytometry systems.

The following Examples are being submitted to illustrate embodiments of the present disclosure. These Examples are intended to be illustrative only and are not intended to limit the scope of the present disclosure. Also, parts and percentages are by weight unless otherwise indicated.

EXAMPLES

Comparative Example 1

In this example, a known hypotonic lytic reagent was used that served both as a lytic agent and as sheath fluid. The reagent utilized was commercially available from IDEXX Laboratories, Inc. in relation to its LaserCyte® instrument. The osmolality of the lytic reagent was about 23 mOsm. The lytic reagent was combined with a dog blood sample, using the standard automated method by which LaserCyte operates. FIG. 1 shows dot plot results of EXT vs. RAS for this control sample. As can be seen in FIG. 1, a significant number of degraded white cells remained overlapped with the rest of the leukocyte population. In particular, the region marked as R8 overlapped with the lymphocyte population and thus had the potential to inaccurately report the lymphocyte count in the sample.

Example 1

A lytic reagent system of the present disclosure was prepared using a surfactant, an alkaline metal salt, and a buffer. The lytic reagent system was formulated as follows:

| | |
|---|---|
| $K_2HPO_4$ | 4.6 mM |
| $KH_2PO_4$ | 0.74 mM |
| NaCl | 30 mM |

-continued

| | |
|---|---|
| SDS | 0.01% |
| BSA | 0.1% |
| pH | 7.8 |

An isotonic sheath was also included in the lytic reagent system. The composition of the isotonic sheath was:

| | |
|---|---|
| $NaHCO_3$ | 94.1 mM |
| NaCl | 53 mM |
| Tricine | 10 mM |
| pH | 7.7 |

1 ml lytic reagent was added into 50 µl of a dog blood sample, followed by mixing and incubation for about 8 to 10 seconds. The pH of the lytic reagent system was about 7.8 and the osmolality was about 75 mOsm.

The treated sample was immediately analyzed by a LASERCYTE® hematology analyzer (from IDEXX Laboratories Inc.). The resultant dot plot of EXT versus RAS is depicted in FIG. 2.

Figure 2:
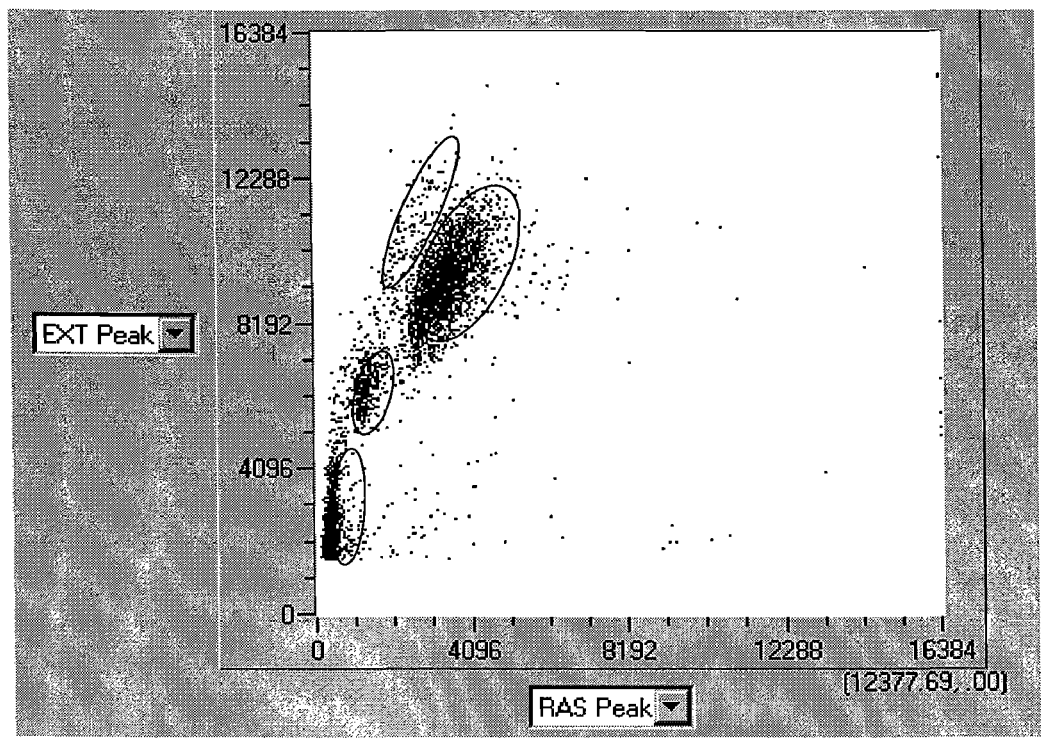
FIGS. 2-5 are dot plot results depicting the components of a blood sample utilizing the reagent system of the present disclosure as described in Examples 1-4.

Compared with the results of Comparative Example 1, there was significantly less debris and ghost cells present after utilizing the lytic reagent system of the present disclosure (as depicted in FIG. 2) compared with the region marked R8 in FIG. 1. Moreover, the absence of degraded cell populations R7 and R8 in FIG. 2 is apparent (compare FIG. 1), with only intact white blood cells separated out in distinct sub-populations after utilizing the lytic reagent system of the present disclosure.

Example 2

A lytic reagent system of the present disclosure was prepared with a stop reagent system of the present disclosure. The lytic reagent system was formulated as follows:

| | |
|---|---|
| $K_2HPO_4$ | 4.6 mM |
| $KH_2PO_4$ | 0.74 mM |
| NaCl | 6.8 mM |
| SDS | 0.01% |
| BSA | 0.1% |
| pH | 7.8 |

The composition of the stop reagent was:

| | |
|---|---|
| NaCl | 200 mM |
| Tris base | 10 mM |
| pH | 7.5 |

50 µl dog blood was incubated with 1 ml of the above lytic reagent for about 10 seconds, and 240 µl of the above stop reagent was then added thereto and mixed with the lytic reagent. The final treated sample was analyzed immediately with a LASERCYTE® hematology analyzer as described above in Example 1.

Figure 3:
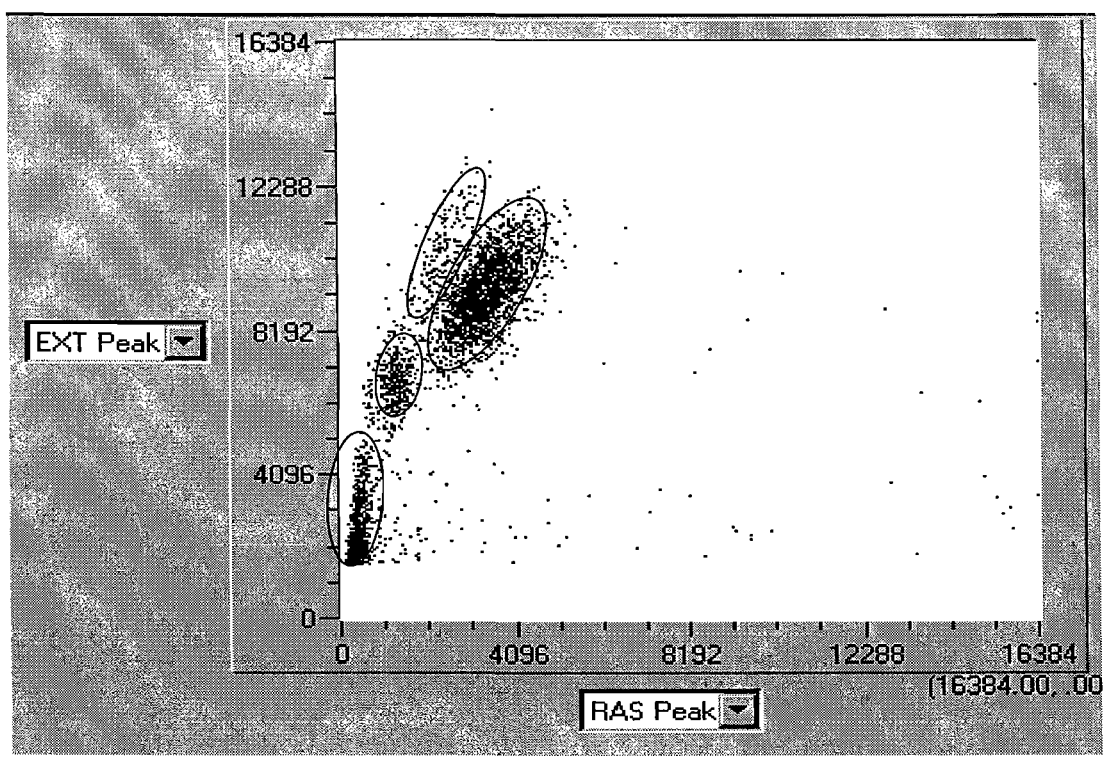

FIG. 3 shows dot plot results of the lytic reagent system. The osmolality was about 25 mOsm and the pH was about 7.8.

Example 3

A lytic reagent system of the present disclosure was prepared without bovine serum albumin as a stabilizer and without a stop reagent. The composition of the lytic reagent system was as follows:

| | |
|---|---|
| $K_2HPO_4$ | 4.6 mM |
| $KH_2PO_4$ | 0.74 mM |
| NaCl | 35 mM |
| SDS | 0.01% |
| pH | 7.8 |

The process of Example 1 was followed. The incubation time of the canine blood sample with the lytic reagent was about 8 to 10 seconds.

Figure 4:
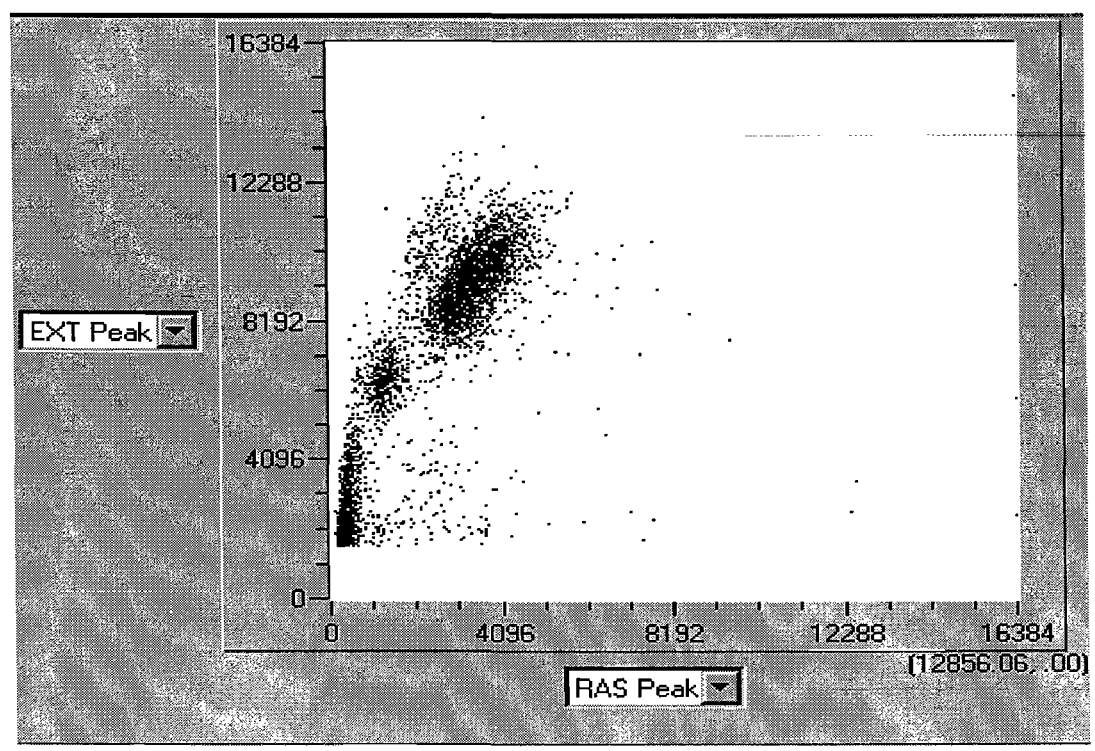

FIG. 4 is a dot plot showing the results obtained with this lytic reagent system. The osmolality was about 80 mOsm.

Example 4

In this example, the stop reagent of Example 2 was used to quench the lytic reaction after a certain time. The general process was the same as described above in Example 2. The composition of the lytic reagent system was as follows:

| | |
|---|---|
| $K_2HPO_4$ | 4.6 mM |
| $KH_2PO_4$ | 0.74 mM |
| NaCl | 6.8 mM |
| SDS | 0.01% |
| pH | 7.8 |

Figure 5:
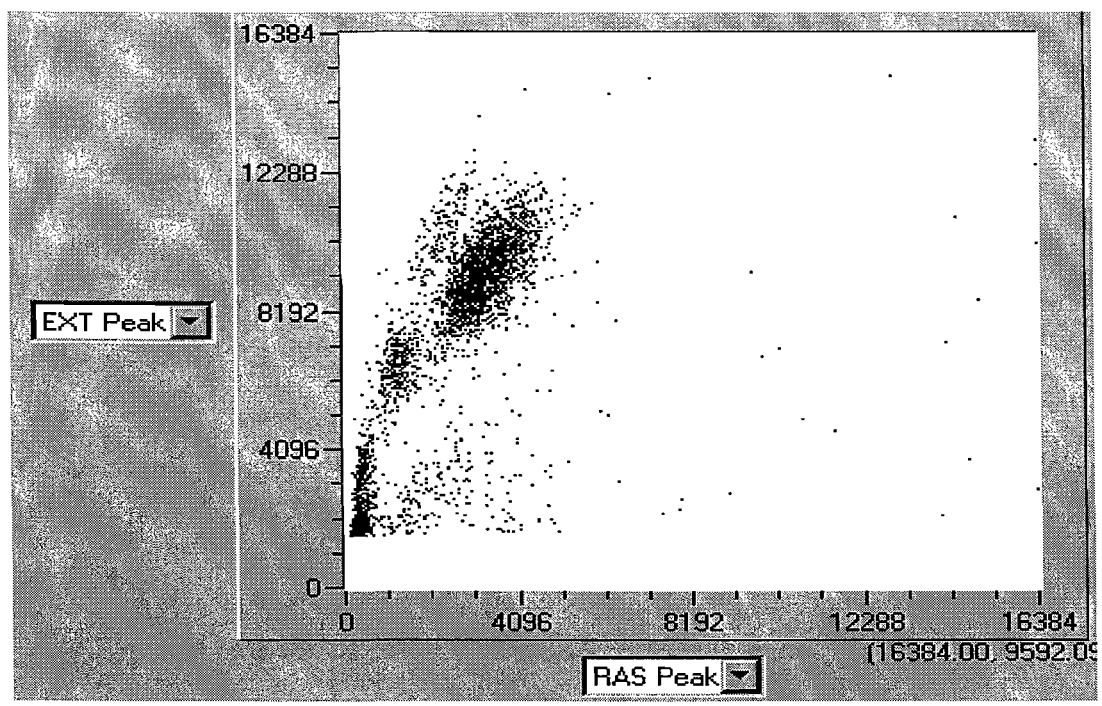

The incubation time of blood with lytic reagent is about 8 to 10 seconds. FIG. 5 is a dot plot of EXT vs. RAS for this lytic reagent system with a canine blood sample. The osmolality was about 25 mOsm.

Example 5

A lytic reagent system was prepared and tested on dog blood as described above in Example 2. The lytic reagent system was as follows:

| | |
|---|---|
| $K_2HPO_4$ | 4.6 mM |
| $KH_2PO_4$ | 0.74 mM |
| NaCl | 6.8 mM |
| SDS | 0.01% |
| BSA | 0.1% |
| pH | 7.6, 11 |

Data was obtained as described above in Example 2, i.e., using a LASERCYTE® hematology analyzer (from IDEXX Laboratories Inc.). The pH of the lytic reagent system was varied by NaOH. Two separate blood samples were analyzed: one using the lytic reagent system at a pH of about 7.6, the other using the lytic reagent system at a pH of about 11.

Figure 6A:
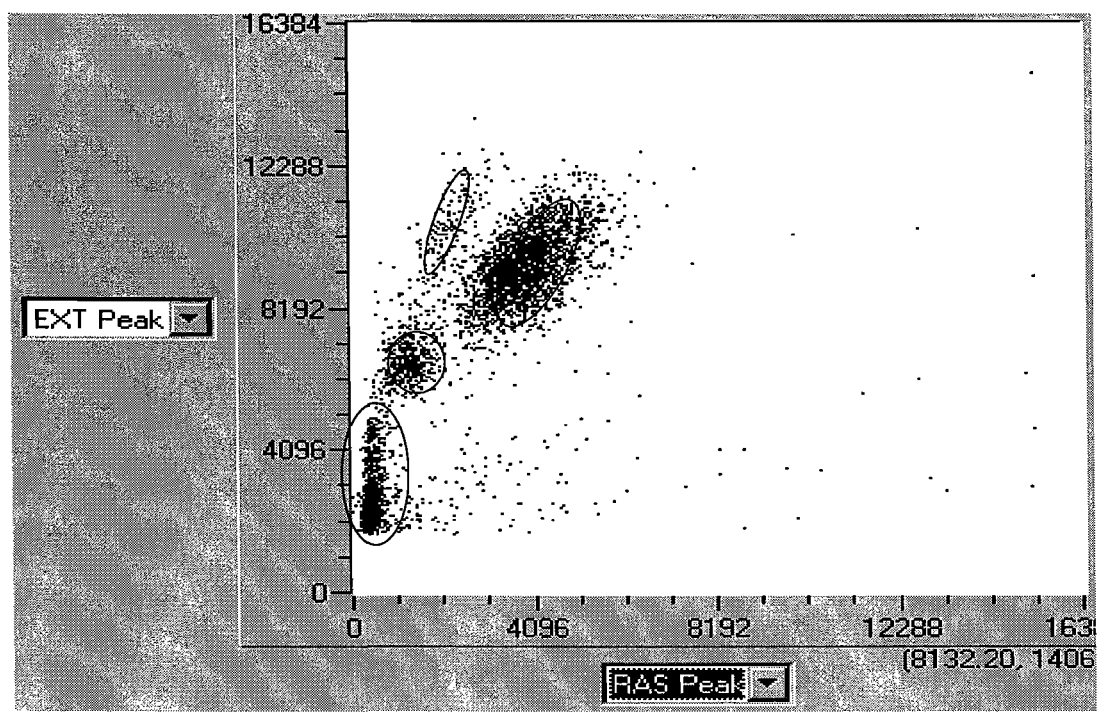
FIGS. 6A and 6B are dot plot results depicting the effect of pH on determining the components of a blood sample utilizing the reagent system of the present disclosure.
Figure 6B:
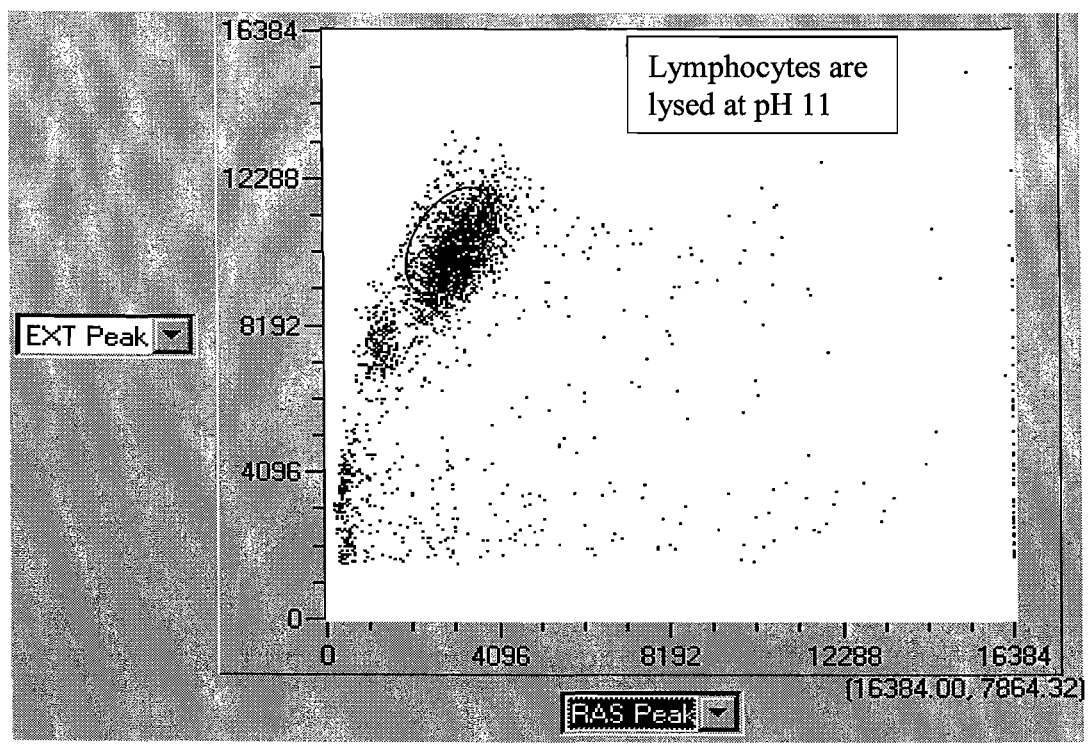

FIGS. 6A and 6B are the dot plot results of EXT vs. RAS showing the effect of pH on the lytic reagent system. FIG. 6A shows the results based on a system where the pH was maintained at about 7.6. As can be seen from the dot plot, there was a significant decrease in the amount of ghost cells between the leukocyte populations and the cells were easily measured. FIG. 6B shows the results based on a system where the pH was maintained at about 11. As can be seen from FIG. 6B, the eosinophils were not resolved and the lymphocytes were partially lysed.

Example 6

A lytic reagent system was prepared and tested on dog blood as described above in Example 2. The lytic reagent system was as follows:

| | |
|---|---|
| $K_2HPO_4$ | 4.6 mM |
| $KH_2PO_4$ | 0.74 mM |
| NaCl | 6.8 mM |
| Sodium Oleate | 0.01% |
| BSA | 0.1% |
| pH | 7.8 |
| $K_2HPO_4$ | 4.6 mM |
| $KH_2PO_4$ | 0.74 mM |
| NaCl | 6.8 mM |
| Sodium Myristate | 0.01% |
| BSA | 0.1% |
| pH | 7.8 |
| $K_2HPO_4$ | 4.6 mM |
| $KH_2PO_4$ | 0.74 mM |
| NaCl | 6.8 mM |
| Sodium Octyl sulfate | 0.01% |
| BSA | 0.1% |
| pH | 7.8 |

Data was obtained as described above in Example 2, i.e., using a LASERCYTE® hematology analyzer (from IDEXX Laboratories Inc.). The surfactants utilized in the lytic reagent system were varied: one utilized sodium oleate; a second utilized sodium myristate, and a third utilized sodium octyl sulfate.

Figure 7A:
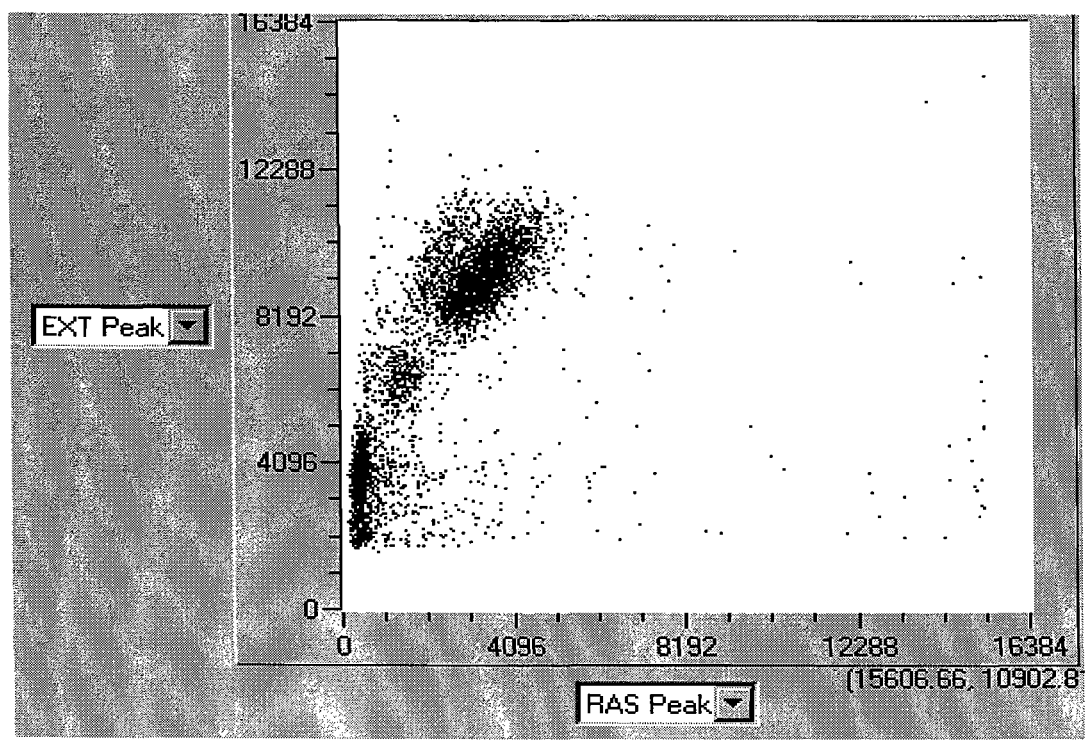
FIGS. 7A, 7B and 7C are dot plot results depicting the components of a blood sample utilizing the reagent system of the present disclosure and various surfactants.
Figure 7B:
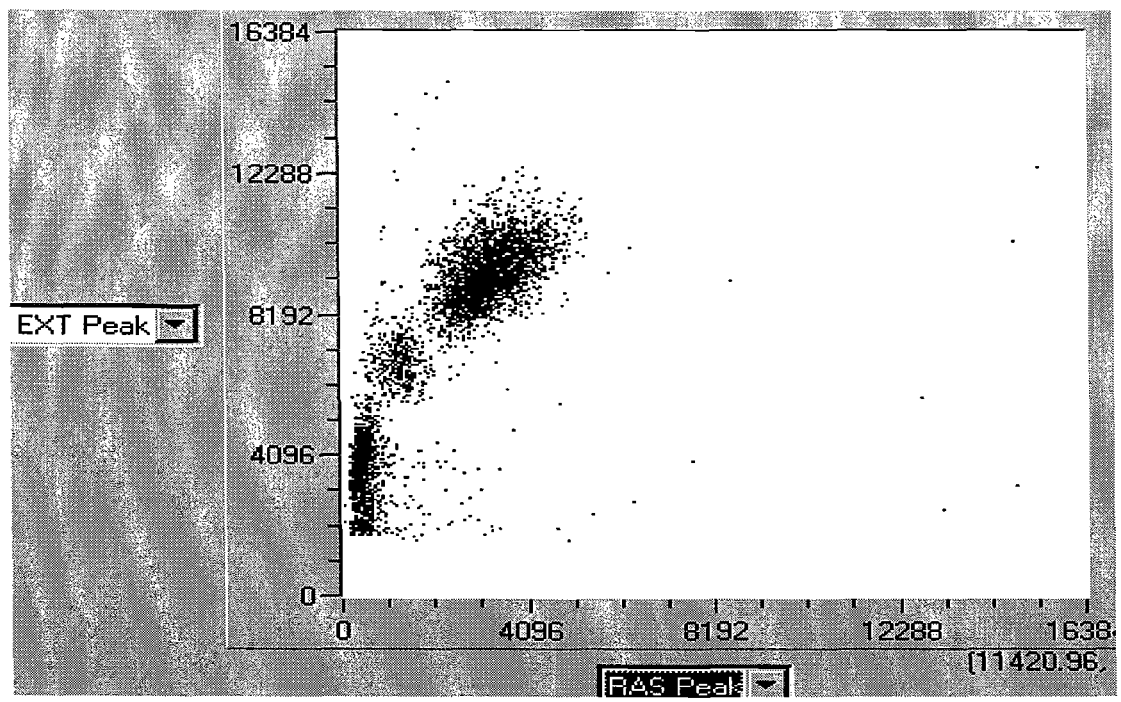
Figure 7C:
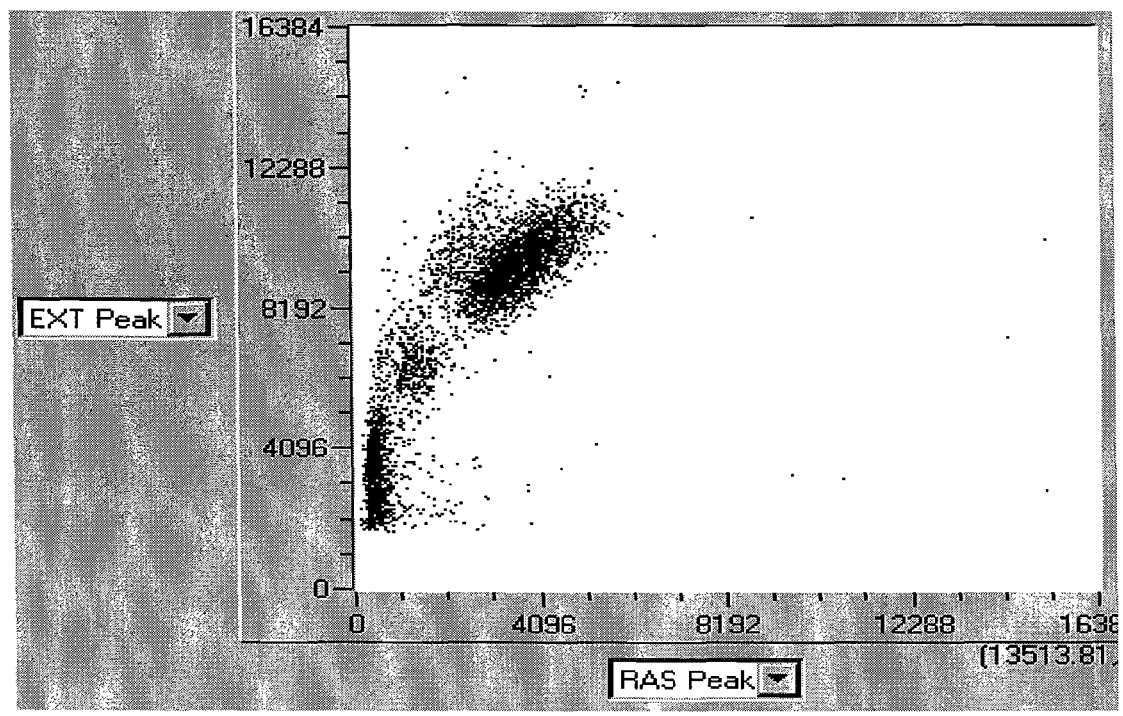

In FIGS. 7A-7C, dot plot results of EXT vs. RAS are shown measuring the effect using different surfactants of the present disclosure. FIG. 7A shows the results based on a system where the surfactant used was sodium oleate. FIG. 7B shows the results based on a system where the surfactant used was sodium myristate: as can be seen in FIG. 7B, it was difficult to resolve the eosinophils population. FIG. 7C shows the results based on a system where the surfactant used was sodium octyl sulfate: as can be seen in FIG. 7C, the eosinophils population was more resolved from any debris.

It will be appreciated that various of the above-disclosed and other features and functions, or alternatives thereof, may be desirable combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A lytic reagent system for use in the determination of a differential white blood cell count consisting essentially of:
   an anionic surfactant at a concentration of from about 0.005 wt % (w/v) to about 0.015 wt % (w/v);
   an alkaline metal salt to adjust osmolality of the system from about 15 mOsm to about 150 mOsm selected from the group consisting of alkaline halides, alkaline chlorides, alkaline bromides, alkaline iodides, and combinations thereof;
   a buffer to maintain a pH of the system from about 6 to about 10;

wherein the lytic reagent system lyses red blood cells in a sample of whole blood at temperatures of up to about 35° C.

2. The lytic reagent system according to claim 1, wherein the alkaline metal salt is used to adjust the osmolality of the system from about 25 mOsm to about 100 mOsm.

3. The lytic reagent system according to claim 1, wherein the buffer maintains the pH of the system from about 7 to about 9.

4. The lytic reagent system according to claim 1, wherein the anionic surfactant is selected from the group consisting of alkaline alkyl carbonates, alkaline alkyl phosphates and alkaline alkyl sulfates.

5. The lytic reagent system according to claim 4, wherein the alkaline alkyl sulfate is selected from the group consisting of sodium octyl sulfate and sodium dodecyl sulfate.

6. The lytic reagent system according to claim 4, wherein the alkaline alkyl phosphate comprises polyether phosphate ester.

7. The lytic reagent system according to claim 4, wherein the alkaline alkyl carbonate comprises sodium oleate.

8. The lytic reagent system according to claim 1, wherein the alkaline metal salt includes an alkaline ion selected from the group consisting of lithium, sodium and potassium.

9. The lytic reagent system according to claim 1, wherein the anionic surfactant includes an alkyl chain containing from about 8 to about 14 carbons.

10. The lytic reagent system according to claim 1, wherein the buffer is selected from the group consisting of phosphate and tris buffers having a concentration from about 2 mM to about 10 mM.

11. The lytic reagent system according to claim 1, further comprising a white blood cell stabilizer.

12. The lytic reagent system according to claim 11, wherein the white blood cell stabilizer comprises bovine serum albumin having a concentration from about 0.01 wt % to about 0.2 wt %.

13. A method for resolving white blood cell sub-populations in a whole blood sample, comprising:
  providing a whole blood sample;
  incubating the whole blood sample with a lytic reagent sufficient such that red blood cells become lysed, the lytic reagent comprising:
    an anionic surfactant,
    an alkaline metal salt to adjust osmolality of the reagent and blood sample from about 15 mOsm to about 150 mOsm, and
    a buffer to maintain a pH of the reagent and blood sample from about 6 to about 10;
  wherein the lytic reagent system lyses red blood cells in the whole blood cell sample at temperatures of up to about 35° C.
  adding a stop solution for a discontinuing a lytic reaction;
  measuring a response from at least two optical detectors as the white blood cells pass through a sensing region in a flow cell of an optical detection system, wherein at least one detector of the at least two detectors measures light scatter at a range of angles whose axis is generally orthogonal to a direction of propagation of a laser beam; and
  differentiating white blood cells in the whole blood sample.

14. The method according to claim 13, wherein the step of adding a stop solution includes contacting the whole blood sample and lytic reagent with a hypertonic solution.

15. The method according to claim 14, wherein the hypertonic solution comprises an alkaline metal salt possessing an alkaline ion selected from the group consisting of sodium, potassium and lithium.

16. The method according to claim 13, wherein at least one of the at least two detectors measures optical response to a laser beam in the sensing region.

17. The method according to claim 13, wherein at least one detector of the at least two detectors measures axial light loss or extinction.

18. The method according to claim 13, wherein the whole blood sample is derived from an animal.

19. The method according to claim 18, wherein the whole blood sample is derived from an animal selected from the group consisting of bovine, canine, equine, ferret and human.

20. The method according to claim 13, wherein the anionic surfactant is selected from the group consisting of alkaline alkyl carbonates, alkaline alkyl phosphates and alkaline alkyl sulfates.

21. The method according to claim 20, wherein the alkaline alkyl sulfate is selected from the group consisting of sodium octyl sulfate and sodium dodecyl sulfate, the alkaline alkyl phosphate comprises polyether phosphate ester, the alkaline alkyl carbonate comprises sodium oleate.

22. The method according to claim 13, wherein the buffer is selected from the group consisting of phosphate and tris buffers having a concentration from about 2 mM to about 10mM.

23. The method according to claim 13, wherein the lytic reagent includes a white blood cell stabilizer which includes bovine serum albumin having a concentration from about 0.01 wt % to about 0.2 wt %.

* * * * *